United States Patent
Hochrainer et al.

[11] Patent Number: 5,947,118
[45] Date of Patent: Sep. 7, 1999

[54] CAPSULE HOLDER

[75] Inventors: Dieter Hochrainer, Ingelheim, Germany; Ross Kinneir, Clifton, United Kingdom

[73] Assignee: Boehringer Ingelheim KG, Ingelheim, Germany

[21] Appl. No.: 08/884,738

[22] Filed: Jun. 30, 1997

Related U.S. Application Data

[62] Division of application No. 08/564,338, filed as application No. PCT/EP94/01751, May 28, 1994, abandoned.

[30] Foreign Application Priority Data

Jun. 3, 1993 [DE] Germany ............................. 43 18 455

[51] Int. Cl.⁶ ................................................... A61M 16/00
[52] U.S. Cl. ............................... 128/203.15; 128/203.12; 128/203.21; 206/539
[58] Field of Search ......................... 128/203.15, 203.12, 128/203.19, 203.21; 604/58; 206/539, 528, 446

[56] References Cited

U.S. PATENT DOCUMENTS

| | | | |
|---|---|---|---|
| 2,037,201 | 4/1936 | Rowntree | 206/306 |
| 2,366,886 | 1/1945 | Van Tuyl | 206/539 |
| 3,606,007 | 9/1971 | Huston, Jr. | 206/528 |
| 3,888,252 | 6/1975 | Side et al. | 128/203.15 |
| 4,117,884 | 10/1978 | James | 128/203.15 |
| 4,206,758 | 6/1980 | Hallworth et al. | 128/203.15 |
| 4,884,565 | 12/1989 | Cocozza | 128/203.15 |
| 4,889,114 | 12/1989 | Kladders | 128/203.15 |

FOREIGN PATENT DOCUMENTS

| | | | |
|---|---|---|---|
| 1501968 | 11/1967 | France . | |
| 2216806 | 8/1974 | France . | |
| 2418161 | 9/1979 | France . | |
| 221414 | 2/1960 | Germany . | |
| 1934956 | 2/1966 | Germany . | |
| 3927170 | 2/1991 | Germany . | |
| 1648842 | 4/1989 | U.S.S.R. | 206/528 |
| 2064334 | 6/1981 | United Kingdom . | |
| 2064336 | 6/1981 | United Kingdom . | |
| 8201470 | 5/1982 | WIPO | 128/203.15 |
| 9406498 | 3/1994 | WIPO | 128/203.12 |

*Primary Examiner*—John G. Weiss
*Assistant Examiner*—V. Srivastava
*Attorney, Agent, or Firm*—Robert P. Raymond; Alan R. Stempel; Anthony P. Bottino

[57] ABSTRACT

A capsule holder for the insertion and fixing of pharmaceutical capsules consists of a plate (2) with a recess (1) in which there are at least three ribs (3) arranged parallel to the central axis and at unequal spacings from one another, between which the capsules can be clamped both by their upper part and by their lower part in such a way that they do not fall out during normal handling but can readily be removed.

21 Claims, 2 Drawing Sheets

5,947,118

CAPSULE HOLDER

This a division of application Ser. No. 08/564,338, filed Apr. 23, 1996, now abandoned which is a 371 of PCT/EP 94/01751 of 05/28/94.

BACKGROUND OF THE INVENTION

The invention relates to a capsule holder for conventional pharmaceutical capsules, particularly for use in conjunction with inhalers in which capsules filled with micronised drug preparation are used.

Inhalers for powder inhalation, by means of which powdered drugs can be inhaled from capsules, are widely used. The older versions were designed so that they could hold only one capsule (DE-A 14 91 715; DE-A 33 45 722).

In order to make refilling easier for the patient, inhalers were later developed in which a number of capsules could be stored (e.g. DE-A 39 27 170). The chambers or recesses intended to hold the capsules have a larger diameter than the capsules.

When the inhaler is open, the capsules can easily fall out during handling, as they are not fixed in the individual chambers. In asthma attacks, in particular, when the patient wishes to inhale rapidly, it is a problem if the capsules are lying loose in the inhaler, as the patient also has to take care to ensure that the capsules do not fall out of the device during use. On the other hand, it is desirable that the empty capsules be removed immediately after use without at the same time allowing the full capsules to fall out, so that it is easy to tell how big a supply of full capsules is still present in the device.

BRIEF SUMMARY OF INVENTION

The invention now proposes a capsule holder which, on the one hand, fixes the capsules in such a way that they do not fall out during normal handling, but on the other hand enables them to be removed easily, irrespective of which end of the capsules has been placed in the recesses.

As is known, the pharmaceutical capsules used for therapeutic purposes consist of two parts; each part is cylindrical in shape and has a hemispherical closure at one end. The internal diameter of th two cylinders is designed so that a relatively firm joint is achieved when the two open ends are fitted together. The external diameters of the two cylindrical parts are different. In a standard commercial size 3 capsule, for example, the diameter of the upper part is 5.83 mm and the diameter of the lower part is 5.57 mm. The capsules consist of a flexible material, preferably hard gelatine.

Cylindrical recesses which fit the external dimensions of the capsules do not solve the problem according to the invention because they are too narrow or too wide for one half of the capsule.

A capsule holder for pharmaceutical capsules has now been developed into which the capsules can be inserted to the same depth with both their upper end and with their lower end, and are on the one hand accommodated firmly enough to prevent them falling out, but on the other hand still remain easily removable so that the parts of the capsules are not accidentally pulled apart on removal.

The holder according to the invention consists of a recess into which the capsule is inserted in the direction of its longitudinal axis, the wall of the recess having at least three ribs arranged parallel to the longitudinal axis and at unequal spacings from one another, the capsule being clamped between these ribs with some deformation.

A capsule holder of this kind is shown in FIGS. 1 to 6.

Figure 1:
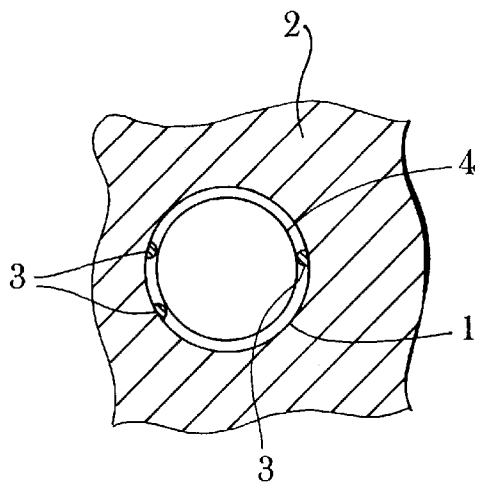
FIG. 1 Cross-section through capsule holder.

FIG. 1 shows a cross-section through a capsule holder according to the invention. The recess 1 of circular cross-section in the plate 2 has three ribs 3, two of which are arranged relatively close together and the third is located opposite. Between the ribs a circle 4 can be inscribed the diameter of which is slightly less than the external diameter of the lower (thinner) part of the capsule. When inserted between the ribs the capsule is slightly deformed. Advantageously, the ribs are rounded off or chamfered at their outer end to make it easier to insert the capsules and prevent damage to the capsules when they are inserted.

The cross-section of the ribs permits many numerous variations; it is generally semicircular or rounded but may also be triangular or rectangular, wherein the ribs preferably, but not necessarily, are of equal height. The same is true of the width of the ribs The surface by which the capsules and ribs come into contact should be relatively small, so that even after being stored in the holder for long periods the capsule can still be removed easily and does not stick. The recess may taper somewhat, i.e. it may be slightly conical in shape (the height of the ribs being constant); it is also possible for the ribs to be somewhat higher towards the lower end of the recess, so that even then (with a constant cross-section of the recess) there is a reduction in the space between the ribs.

Figure 2B:
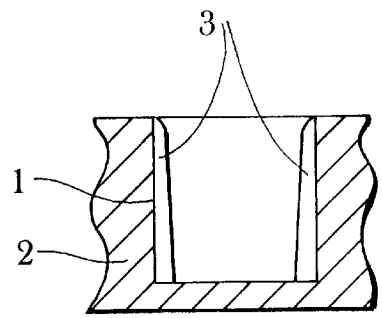
FIG. 2b Vertical-section through ribs.
Figure 2:
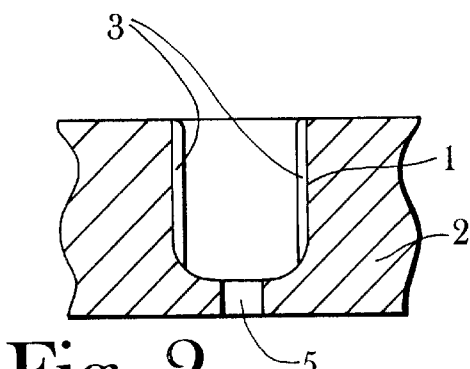
FIG. 2 Vertical-section through capsule holder.

FIG. 2 shows a vertical section along the longitudinal axis of a capsule holder according to the invention, the ribs 3 being visible in the recess 1 in the plate 2.

The recess 1 has, generally at the bottom, an opening 5 which makes cleaning easier.

Figure 2A:
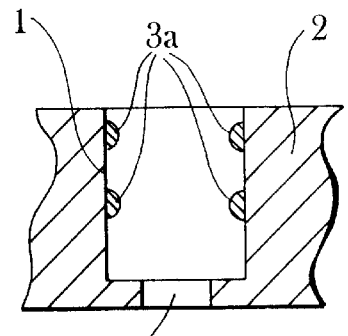
FIG. 2a Cross-section through ribs.

As shown in FIG. 2a, the ribs may also be replaced by a suitable arrangement of bumps 3a.

In FIG. 2b the height of the rib cross-section increases downwardly, 80 that the ribs are at a smaller spacing from one another towards the bottom.

Figure 3:
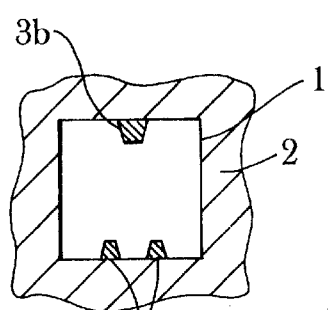
FIG. 3 Capsule holder of rectangular cross-section.

FIG. 3 shows an-example of a capsule holder of rectangular cross-section with a different configuration for the ribs (3b).

Figure 4:
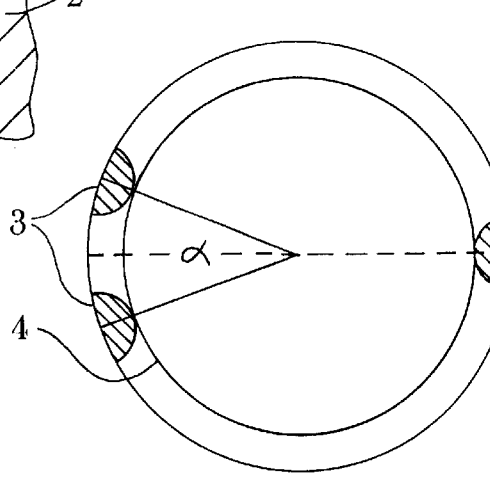
FIG. 4 Arrangement of ribs.

A larger number of ribs are shown in FIG. 4, the ribs 3c being triangular in cross-section.

Figure 5:
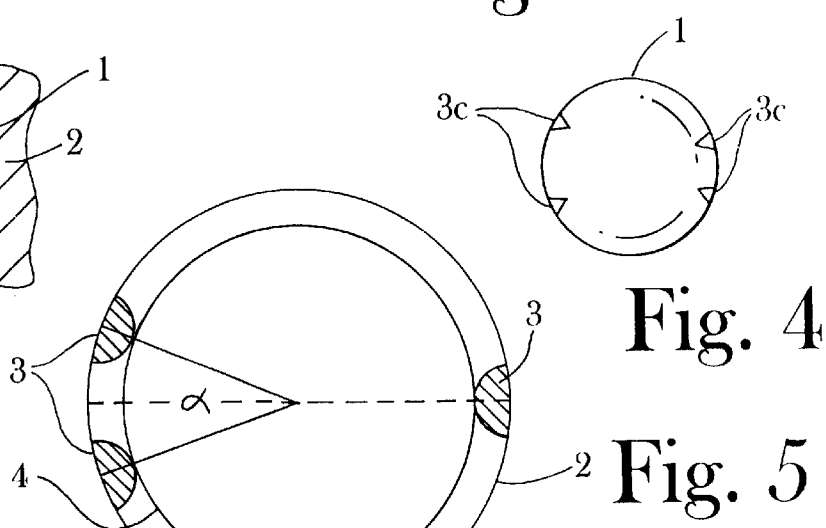
FIG. 5 Another arrangement of ribs.

In order to allow sufficient deformation (the other prerequisites remaining the same) the ribs are not mounted at equal spacings, based on the inscribed circle. This is shown in FIG. 5. The angle α between the two ribs 3 arranged closer together is about 30 to 60°, preferably 35 to 50°. An angle of about 40° has proved particularly suitable. The opposite rib is located on the diameter which bisects the angle α or is offset slightly to one side. At an angle of 40°, for example, the capsule centers itself on being inserted, whilst if the angle is too small it may be located in an oblique position, with the result that, in some cases, removal may be prevented, particularly when a number of holders are provided side by side.

Figure 6:
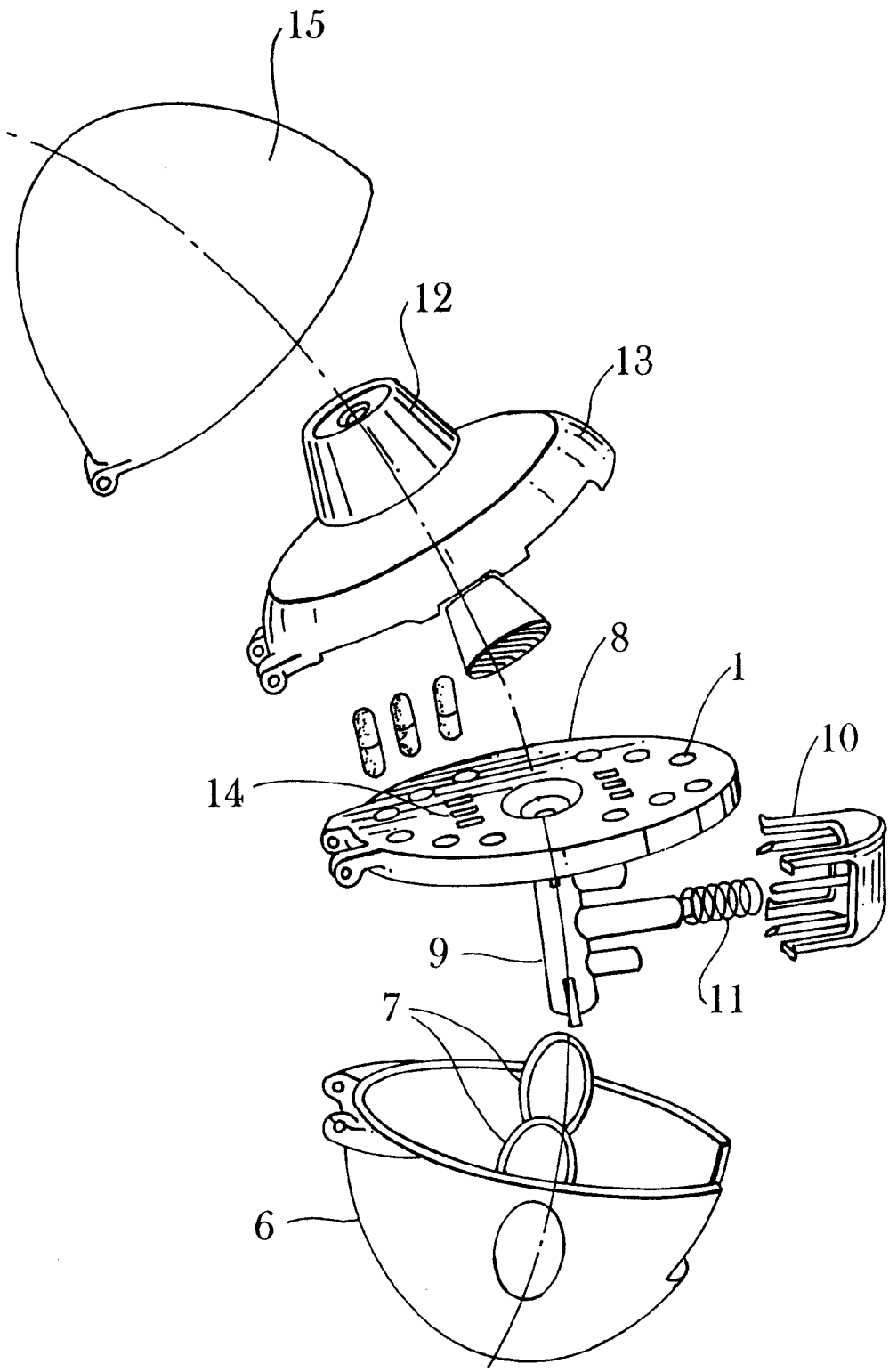
FIG. 6 Inhaler.

FIG. 6 shows the possible construction of an inhaler incorporating the capsule holders according to the invention.

In a lower part 6 having two windows 7 is a plate a which is connected to the inhalation chamber 9 and which also contains 12 capsule holders 1. The button 10 provided with two specially ground needles serves to open the capsules in the capsule chamber 9; this button is pressed in counter to the pressure of the spring 11 and thereby cuts open or pierces the capsule in the chamber at two points. When the user inhales through the device by means of the mouthpiece 12 connected to the upper part 13, the air passes through the openings 14 into the lower part 6 and from there at the lower end into the capsule chamber 9, which is constructed like the capsule chamber in the inhaler according to DE-A 3927170. The device is closed off by a lid which is connected to the lower part 6, the plate 8 and the upper part 13 in such a way that it can be flipped shut so that, once the lid is closed, no dust can enter the device.

We claim:

1. An inhaler device comprising:
    an upper part and a lower part;
    a capsule holder comprising a plate with a recess, the recess having an open end and a closed end, having walls parallel to a central axis and being at a spacing from one another which is greater than the maximum capsule diameter, the walls having at least three ribs running parallel to the central axis and at unequal spacing from one another, the ribs having surfaces or edges oriented towards the central axis defining an inscribed cylinder, the diameter of the inscribed cylinder being smaller than the diameter of the lower part of the capsule.

2. The inhaler according to claim 1, wherein the recess is cylindrical and has three ribs, two of the ribs being located adjacent to one another and the third rib being arranged opposite the central line between the other two ribs.

3. The inhaler according to claim 2, wherein the angle formed by the radii extending to the center of the first two ribs is 30–60°.

4. The inhaler according to claim 3, wherein the angle is between 35–50°.

5. The inhaler according to claim 4, wherein the angle is about 40°.

6. The inhaler according to claim 1, wherein the ribs are rounded off or angled towards the center of the recess.

7. The inhaler according to claim 1, wherein the height of the ribs increases downwardly so that the surfaces or edges directed towards the central axis define an inscribed truncated cone which has its maximum diameter at the open end of the recess.

8. The inhaler according to claim 1, wherein the ribs are rounded off or chamfered at there outer ends.

9. The inhaler according to any one of claims 2–8 or 1, wherein the lower part comprises a capsule chamber with two windows and a plate which is connected to an inhaler chamber.

10. The inhaler according to claim 9, wherein the inhaler has twelve capsule holders.

11. The inhaler according to claim 10, further comprising a button connected to a ground needle such that when the button is pressed, the capsules in the capsule chamber are pierced by the needle.

12. The inhaler according to claim 11, having two ground needles such that when the button is pressed, the capsules in the capsule chamber are pierced in two points.

13. The inhaler according to claim 8, further comprising a mouthpiece connected to the upper part of the inhaler such that when the user inhales through the mouthpiece, air passes into the lower part of the inhaler and into the capsule chamber.

14. The inhaler according to claim 13, further comprising a lid which is connected to the inhaler such that the lid can be flipped shut.

15. A capsule holder comprising a plate with a recess, the recess having an open end and a closed end, having walls parallel to the central axis and being at a spacing from one another which is greater than the maximum capsule diameter, the walls having at least three ribs running parallel to the central axis and at unequal spacing from one another, the ribs having surfaces or edges oriented towards the central axis defining an inscribed cylinder, the diameter of the inscribed cylinder being smaller than the diameter of the lower part of the capsule.

16. The capsule holder according to claim 15, wherein the recess is cylindrical and has three ribs, two of the ribs being located adjacent to one another and the third rib being arranged opposite the central line between the two adjacent ribs.

17. The capsule holder according to claim 16, wherein the angle formed by the radii extending to the center of the two adjacent ribs is 30° to 60°.

18. The capsule holder according to claim 17, wherein the angle is 35° to 50°.

19. The capsule holder according to claim 18, wherein the angle is about 40°.

20. The capsule holder according to claim 1 or 15, wherein the ribs are rounded off or angled towards the center of the recess.

21. A capsule holder comprising a plate with a recess, the recess having an open end and a closed end, having walls parallel to the central axis and being at a spacing from one another which is greater than the maximum capsule diameter, the walls having at least three ribs running parallel to the central axis and at unequal spacing from one another, wherein the height of the ribs increases downwardly so that the surfaces or edges of the ribs oriented towards the central axis define a truncated cone having its maximum diameter at the open end of the recess.

* * * * *